US010726956B2

United States Patent
Jiang et al.

(10) Patent No.: US 10,726,956 B2
(45) Date of Patent: Jul. 28, 2020

(54) FEVER EPIDEMIC DETECTION SYSTEM AND METHOD THEREOF

(71) Applicant: NATIONAL TAIWAN UNIVERSITY, Taipei (TW)

(72) Inventors: Joe-Air Jiang, Taipei (TW); Chien-Hao Wang, Taipei (TW); Ya-An Chan, Taipei (TW); Lin-Kuei Su, Taipei (TW); Cheng-Yue Liu, Taipei (TW); Po-Han Chen, Taipei (TW); Wei-Sheng Chen, Taipei (TW); Ching-Ya Tseng, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 7 days.

(21) Appl. No.: 15/130,572

(22) Filed: Apr. 15, 2016

(65) Prior Publication Data
US 2018/0046778 A1 Feb. 15, 2018

(30) Foreign Application Priority Data
Dec. 28, 2015 (TW) .................................. 104144034

(51) Int. Cl.
*G16H 50/80* (2018.01)
*G16H 40/40* (2018.01)
(Continued)

(52) U.S. Cl.
CPC ............... *G16H 50/80* (2018.01); *A61B 5/01* (2013.01); *A61B 5/746* (2013.01); *G06Q 50/22* (2013.01);
(Continued)

(58) Field of Classification Search
CPC .......... G16H 50/80; G16H 40/40; A61B 5/01; A61B 5/745; A61B 2560/0223;
(Continued)

(56) References Cited

U.S. PATENT DOCUMENTS

2009/0105605 A1\* 4/2009 Abreu ................. A61B 5/0008
600/549
2009/0136093 A1\* 5/2009 Hartlove ............ G06K 9/00369
382/110
(Continued)

FOREIGN PATENT DOCUMENTS

| CN | 2012101877721 | 6/2012 |
| TW | 100135408 | 9/2011 |
| TW | 102221174 | 11/2013 |

OTHER PUBLICATIONS

Li Wang, Sze Wey Chua, and Victor Tan, Apr. 12, 2004, "Types of thermal imaging systems for mass fever screening and their evaluations", Proc. SPIE 5405, Thermosense XXVI, pp. 79-87. (Year: 2004).\*

*Primary Examiner* — Christopher L Gilligan
(74) *Attorney, Agent, or Firm* — Aeon Law, PLLC; Adam L. K. Philipp; Martin Spencer Garthwaite

(57) ABSTRACT

The fever epidemic detection system comprises a detection module, a control module and a communication module. The detection module measures and obtains a body-temperature measured value. The control module comprises a first operation unit, a determination unit and an alert unit. The first operation unit receives and calibrates the body-temperature measured value with a calibration factor, and generates a body-temperature calibrated value. The determination unit receives and determines whether the body-temperature calibrated value is within a preset normal body-temperature range and generates a determination result. The alert unit receives the determination result. The communication module transmits data to an external device. The alert unit generates a first alerting message, if the determination result shows that the body-temperature calibrated value is not within a preset normal body-temperature range. The control module transmits the first alerting message and the corresponding body-temperature to the external device via the communication module.

3 Claims, 7 Drawing Sheets

(51) Int. Cl.
*G06Q 50/22* (2018.01)
*A61B 5/01* (2006.01)
*A61B 5/00* (2006.01)

(52) U.S. Cl.
CPC ............ *G16H 40/40* (2018.01); *A61B 5/0077* (2013.01); *A61B 2505/01* (2013.01); *A61B 2560/0223* (2013.01); *A61B 2560/0252* (2013.01)

(58) Field of Classification Search
CPC .............. A61B 5/0077; A61B 2505/01; A61B 2560/0252; G06Q 50/22
See application file for complete search history.

(56) References Cited

U.S. PATENT DOCUMENTS

2014/0292517 A1\* 10/2014 Hu ........................... A61B 5/00
  340/573.1
2014/0320648 A1\* 10/2014 Sager ...................... H04Q 9/00
  348/143

\* cited by examiner

FEVER EPIDEMIC DETECTION SYSTEM AND METHOD THEREOF

BACKGROUND OF THE INVENTION

1. Field of the Invention

The instant disclosure relates to a fever epidemic detection system and a fever epidemic detection method; in particular, to a fever epidemic detection system and a fever epidemic detection method that automatically and widely detect the fever epidemic in a region via a thermal imager and the Internet of Things (IoT).

2. Description of Related Art

In order to detect and prevent the fever epidemic, it is necessary to install a fever epidemic detection system for detecting the temperature of people passing through some crowded regions like the airport lobby, hospital lobby, multi-story office building, department store and the like. The current fever epidemic detection systems detect people's temperatures via a contacting detection or a non-contacting detection which are both effective. With respect to the contacting detection, there are lots of labor cost and time needed. On the other hand, with respect to the conventional non-contacting detection, it is convenient to detect one's temperature without contacting his body, but it is still necessary for the supervisor to spend time checking whether the region under detection is possible to be or has already been critical once there is a person found to have an abnormal temperature. The current non-contacting detection also takes lots of labor cost and time, and thus it cannot help the supervisor to determine the current status of the region under detection or to effectively predict the spread of the fever epidemic.

SUMMARY OF THE INVENTION

The instant disclosure provides a fever epidemic detection system that can automatically and widely detect the fever epidemic in a region via the Internet of Things. The fever epidemic detection system comprises a detection module, a control module and a communication module. The detection module measures temperature of each person in the region and obtains a measured temperature, wherein the detection module comprises at least one thermal imager. The control module is connected to the detection module, and the control module comprises a first operation unit, a determination unit and an alert unit. The first operation unit receives and calibrates the measured temperature with a calibration factor to calculate a calibrated temperature, wherein the calibration factor is related to the detection module. The determination unit is connected to the first operation unit, receives the calibrated temperature, and determines whether the calibrated temperature is within a normal temperature range for generating a determination result. The alert unit is connected to the determination unit and receives the determination result. The communication module is connected to the control module and the detection module, and transmits data to an external device. The alert unit generates a first alerting message if the determination result indicates that the calibrated temperature is not within the normal temperature range. After that, the control module transmits the first alerting message and the corresponding calibrated temperature to an external device via the communication module.

The instant disclosure further provides a fever epidemic detection method used in a fever epidemic detection system, for automatically and widely detecting the fever epidemic in a region via the Internet of Things. The fever epidemic detection system comprises a detection module, a control module and a communication module. The control module is connected to the detection module, and the communication module is connected to the control module. The detection module comprises at least one thermal imager. The control module comprises a first operation unit, a second operation unit, a determination unit, an alert unit and a sensing unit. The determination unit is connected to the first operation unit. The alert unit and the sensing unit are both connected to the determination unit, and the second operation unit is connected to the alert unit. The fever epidemic detection method comprises: measuring temperature of each person in the region to obtain a measured temperature; calibrating the measured temperature with a calibration factor to calculate a calibrated temperature, wherein the calibration factor is related to the detection module; determining whether the calibrated temperature is within a predetermined normal temperature range to generate a determination result; and generating a first alerting message and outputting the first alerting message and the corresponding calibrated temperature if the determination result indicates that the calibrated temperature is not within the normal temperature range.

To sum up, via the combination of the detection module (e.g. a thermal imager), the control module and the Internet of Things (IoT), the fever epidemic detection system and the method thereof provided by the instant disclosure can not only automatically detect the temperatures of people, but also can simultaneously execute the data operation and determine whether there is any abnormal situation. In addition, the fever epidemic detection system and the method thereof can transmit the alerting message indicating the abnormal situation and the corresponding data to an external device via the IoT. Thereby, the supervisor can know in real time that the region under detection is safe, is possible to be or has already been critical. In other words, it only takes little labor cost for the fever epidemic detection system and the method thereof provided by the instant disclosure to immediately predict the spread of the fever epidemic and to further stop the disease from spreading as soon as possible.

For further understanding of the instant disclosure, reference is made to the following detailed description illustrating the embodiments and embodiments of the instant disclosure. The description is only for illustrating the instant disclosure, not for limiting the scope of the claim.

BRIEF DESCRIPTION OF THE DRAWINGS

Embodiments are illustrated by way of example and not by way of limitation in the figures of the accompanying drawings, in which like references indicate similar elements and in which.

DETAILED DESCRIPTION OF PREFERRED EMBODIMENTS

Figure 1:
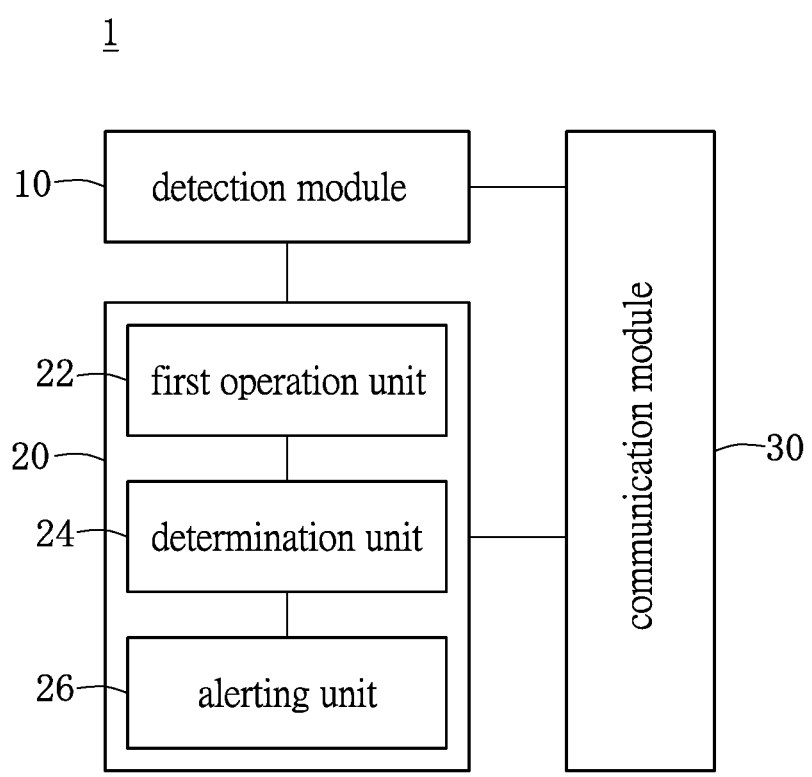
FIG. 1 shows a block diagram of a fever epidemic detection system of one embodiment of the instant disclosure.

The aforementioned illustrations and following detailed descriptions are exemplary for the purpose of further explaining the scope of the instant disclosure. Other objectives and advantages related to the instant disclosure will be illustrated in the subsequent descriptions and appended drawings.

Example embodiments will be described below in more detail with reference to the accompanying drawings. Many different forms and embodiments are possible without deviating from the spirit and teachings of this disclosure and so the disclosure should not be construed as limited to the embodiments set forth herein. Rather, these embodiments are provided so that this disclosure will be thorough and complete, and will fully convey the scope of the disclosure to those skilled in the art. In the drawings, like reference numbers refer to like elements throughout.

The fever epidemic detection system and method thereof provided by the instant disclosure can automatically and widely detect the fever epidemic within a region, and transmit the obtained data to an external device for supervising. The fever epidemic detection system and method have no landform or space constraints. In other words, they can be used in both of a plane area or a multi-story building, such as the airport lobby, station lobby, hospital lobby, multi-story office building or mansion. In the following descriptions, there are several embodiments that can illustrate the fever epidemic detection system and method thereof provided by the instant disclosure.

One Embodiment of the Fever Epidemic Detection System

Refer to FIG. 1. FIG. 1 shows a block diagram of a fever epidemic detection system of one embodiment of the instant disclosure. As mentioned, the fever epidemic detection system has no landform or space constraints. However, for easily understanding, the airport lobby is taken for example as a region under detection, but it is not limited herein.

As shown in FIG. 1, the fever epidemic detection system 1 comprises a detection module 10, a control module 20 and a communication module 30. The control module 20 is connected to the detection module 10, and the communication module 30 is connected to the detection module 10 and the control module 20 for the data transmission with an external device.

Specifically, the fever epidemic detection system 1 in this embodiment is installed in an airport lobby. After measuring the temperature of each person passing through the lobby, the detection module 10 obtains a measured temperature of each person. It is worth mentioning that the detection module 10 comprises at least a thermal imager. Generally, there is always a minor difference between the measured temperature and the actual temperature of a human body. Thus, after receiving the measured temperature of each person obtained by the detection module 10, the first operation unit 20 calculates a calibrated temperature that is much closer to the actual temperature of the detected human body based on the measured temperature of each person and a calibration factor, wherein the calibration factor is related to the detection module 10. That is, there are various calibration factors with respect to different types of the detection module 10 used in the fever epidemic detection system 1. For example, in a case that the detection module 10 comprises a thermal imager, there are different calibration factors with respect to different types of the thermal imagers.

The determination unit 24 determines whether the calibrated temperature is within a predetermined normal temperature range, such as 35° C.~37° C., and then generates and transmits a determination result to an alert unit 26, after the first operation unit 22 calculates the calibrated temperature. If the calibrated temperature is not within the normal temperature range, and the alert unit 26 generates a first alerting message. The first alerting message and the corresponding calibrated temperature are transmitted to an external device via the communication module 30. For example, assumed that the calibrated temperature is 37.5° C., the determination result generated by the determination unit 24 indicates that this calibrated temperature is not within the normal temperature range. Under this circumstance, the alert unit 26 outputs a first alerting message, such as a SMS message or the like, according to the determination result to remind the supervisor of an abnormal situation. Additionally, the alert unit 26 also outputs the corresponding calibrated temperature "37.5° C." as a detailed information for the supervisor.

Thereby, via the fever epidemic detection system in this embodiment, it is able to automatically detect the temperatures of people passing through a region. Once there is an abnormal case found, an alerting message and the corresponding detailed information will be transmitted to an external device via the Internet of Things (IoT). As a result, lots of labor cost can be reduced and any abnormal case can be immediately noticed and dealt with.

For a specific instruction of the fever epidemic detection system provided by the instant disclosure, there is at least one embodiment recited below for further instruction. In the following embodiments, there are only parts different from the embodiment in FIG. 1 described, and the omitted parts are indicated to be identical to the embodiment in FIG. 1. In addition, for an easy instruction, similar reference numbers or symbols refer to elements alike.

Another Embodiment of the Fever Epidemic Detection System

Figure 2:
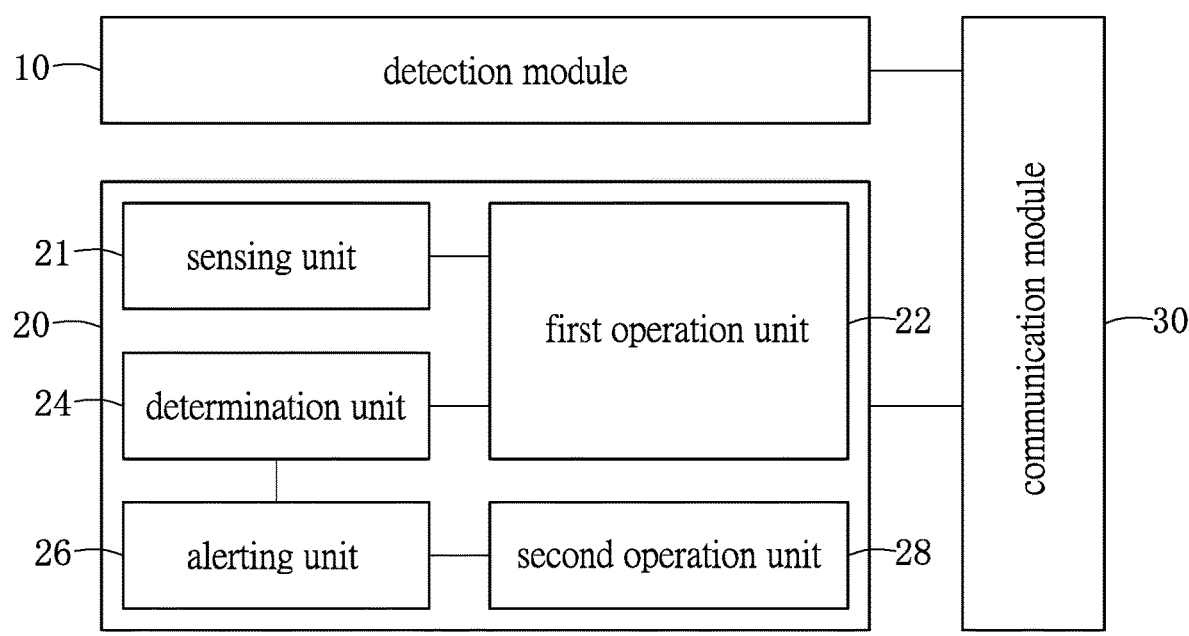
FIG. 2 shows a block diagram of a fever epidemic detection system of another embodiment of the instant disclosure.

Refer to FIG. 2. FIG. 2 shows a block diagram of a fever epidemic detection system of another embodiment of the instant disclosure. The configuration and working principle of the fever epidemic detection system 2 in this embodiment and the fever epidemic detection system 1 in the last embodiment shown in FIG. 1 are alike, but the difference is that, the fever epidemic detection system 2 in this embodiment further comprises a sensing unit 21 and a second operation unit 28. As shown in FIG. 2, the sensing unit 21 is connected to the first operation unit 22, and the second operation unit 28 is connected to the alert unit 26.

Likewise, the fever epidemic detection system 2 has also no landform or space constraints. However, for easily understanding, the airport lobby is taken for example as the detected region, but it is not limited herein.

The fever epidemic detection system 2 is installed in the airport lobby. The detection module 10 obtains a measured temperature of each person, and the first operation unit 22 calculates a calibrated temperature based on the measured temperature and a calibration factor. After that, the determination unit 24 determines whether the calibrated temperature is within a predetermined normal temperature range.

In most cases, the normal temperature range of the human body is influenced by the variation of the environment temperature. For example, in winter days, the environment temperature is generally lower. Thus, the temperature of the human body in winter days is relatively lower than the temperature of the human body in summer days. On the other hand, in summer days, the environment temperature is generally higher. Thus, the temperature of the human body in summer days is relatively higher than the temperature of the human body in winter days. Although the temperature increase and decrease herein are little, but they should not be omitted. Specifically speaking, the normal temperature range of the human body is only two to three degrees. Then, even though the above mentioned temperature increase and decrease are little, how the environment temperature variation will influence the normal temperature range needs to be taken into account for the detection accuracy.

In addition to the environment temperature variation, the normal temperature range of the human body is also affected by the average temperature of all people under detection during each time interval. For instance, if a group of people who have just finished the high-intensity activity, such as running for catching the flight, and these people would have a relatively higher temperature. However, the normal temperature range of the human body is only two to three degrees, so the temperature increase herein will still influence the normal temperature range. Thus, for the detection accuracy, during each time interval, the average temperature of all people under detection needs to be taken into consideration to adjust the normal temperature range.

Considering the influence of the environment temperature and the temperature of all people under detection, in this embodiment, in each predetermined time interval, such as 15 min, the sensing unit 21 detects the temperature of the airport lobby and accordingly calculates an environment average temperature. The sensing unit 21 calculates an environment average temperature parameter based on the environment average temperature, and transmits the environment average temperature parameter to the first operation unit 22. Simultaneously, the operation unit 22 calculates a group average temperature based on the calibrated temperatures of people who have passed through the airport lobby during each time interval. Based on the group average temperature, the operation unit 22 further calculates a group average temperature parameter. Finally, the first operation unit 22 adjusts the normal temperature range according to the environment average temperature parameter and the group average temperature parameter to increase the detection accuracy.

In addition, as described in the last embodiment, the alert unit 26 in this embodiment transmits a first alerting message once finding a person whose temperature is not within the normal temperature range. In this embodiment, to immediately know that the region under detection is safe, possible to be or has already been critical, the second operation unit 28 counts the number of the first alerting messages accumulated during each predetermined time interval, such as 15 min. When the number of the first alerting messages is larger than a predetermined message number, the control module 20 makes the alert unit 26 generate a second alerting message and transmits the second alerting message and the corresponding number of the first alerting messages to an external device via the communication module 30. From the above, the second alerting message indicates that, among the people who has passed through the airport lobby during a time interval, the number of people whose temperature are abnormal is equal to or even more than the predetermined message number. That is, the supervisor can know that the airport lobby is possible to be or has already been critical according to the second alerting message. If there is only the first alerting message transmitted by the alert unit 26, and it indicates that, during a time interval, there are only few people having abnormal temperature among the people who has passed through the airport lobby and thus the supervisor can know that the airport lobby is still a safe region.

However, the number of people passing through the airport lobby varies with time. In other words, in different time intervals, people passing through the airport lobby will be sometimes more or sometimes less. Under the circumstance that there are less people passing through the airport lobby in a time interval, if the number of people whose temperature are abnormal is less than the predetermined message number, but the ratio of the number of people having abnormal temperatures to the total number of people passing through the airport lobby is equal to or even larger than a specific ratio, such as ½, and the airport lobby is still determined to be possible to be or has already been critical.

Thus, in this embodiment, the detection module 10 further calculates and outputs the number of people having passed through the airport lobby during each predetermined time interval, such as 15 min, to the control module 20. Simultaneously, the second operation unit 28 counts the number of the first alerting messages accumulated during each predetermined time interval. After that, after receiving the number of people having passed through the airport lobby, the second operation unit 28 calculates a ratio of the number of the accumulated first alerting messages to the number of people having passed through the airport lobby during the same time interval. If the ratio is equal to or larger than a predetermined ratio, such as ½, the alert unit 26 generates a third alerting message, and the control module 20 transmits the third alerting message, the ratio and the corresponding number of the first alerting messages and the number of people having passed through the airport lobby to an external device via the communication module 30.

In other words, the third alerting message indicates that, among people who have passed through the airport lobby during a predetermined time interval, the people whose temperatures are abnormal are equal to or more than a certain percentage of the people who have passed through the airport lobby. As a result, the airport lobby is possible to be or has already been critical. If there is only the first alerting message transmitted by the alert unit 26, and it indicates that, during a time interval, there are few people having abnormal temperature among the people who has passed through the airport lobby but the airport lobby can be still considered a safe region.

Accordingly, the number of people passing through the airport lobby varies with time, but in this embodiment, alerting functions of the second alerting message and the third alerting message are complementary. For example, in the time interval when there are less people passing through the airport lobby, although the number of people whose temperatures are abnormal is less than the above mentioned predetermined message number, they may still be equal to or more than a certain percentage of the number of people having passed through the airport lobby during this time interval. Thus, the airport lobby is still likely to be or may have already been critical, which is indicated by the second alerting message. For another example, in the time interval when there are more people passing through the airport lobby, although the number of people whose temperatures are abnormal is less than a certain percentage of the number of people having passed though the airport lobby, they may still be equal to or more than the above predetermined message number. Thus, the airport lobby is still likely to be or may have already been critical, which is indicated by the third alerting message.

Figure 3A:
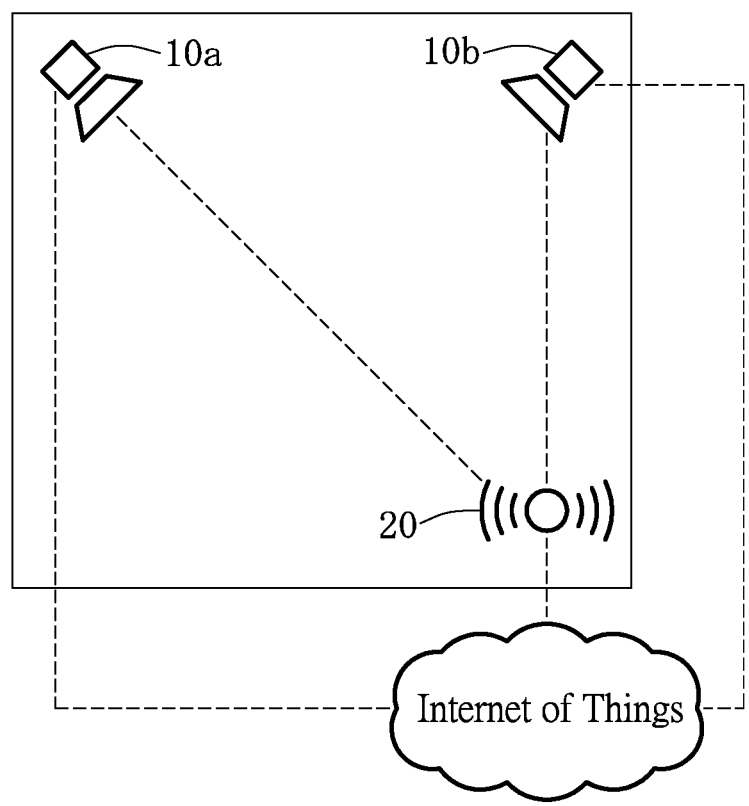
FIG. 3A shows a schematic diagram of the data transmission in a fever epidemic detection system of one embodiment of the instant disclosure.
Figure 3B:
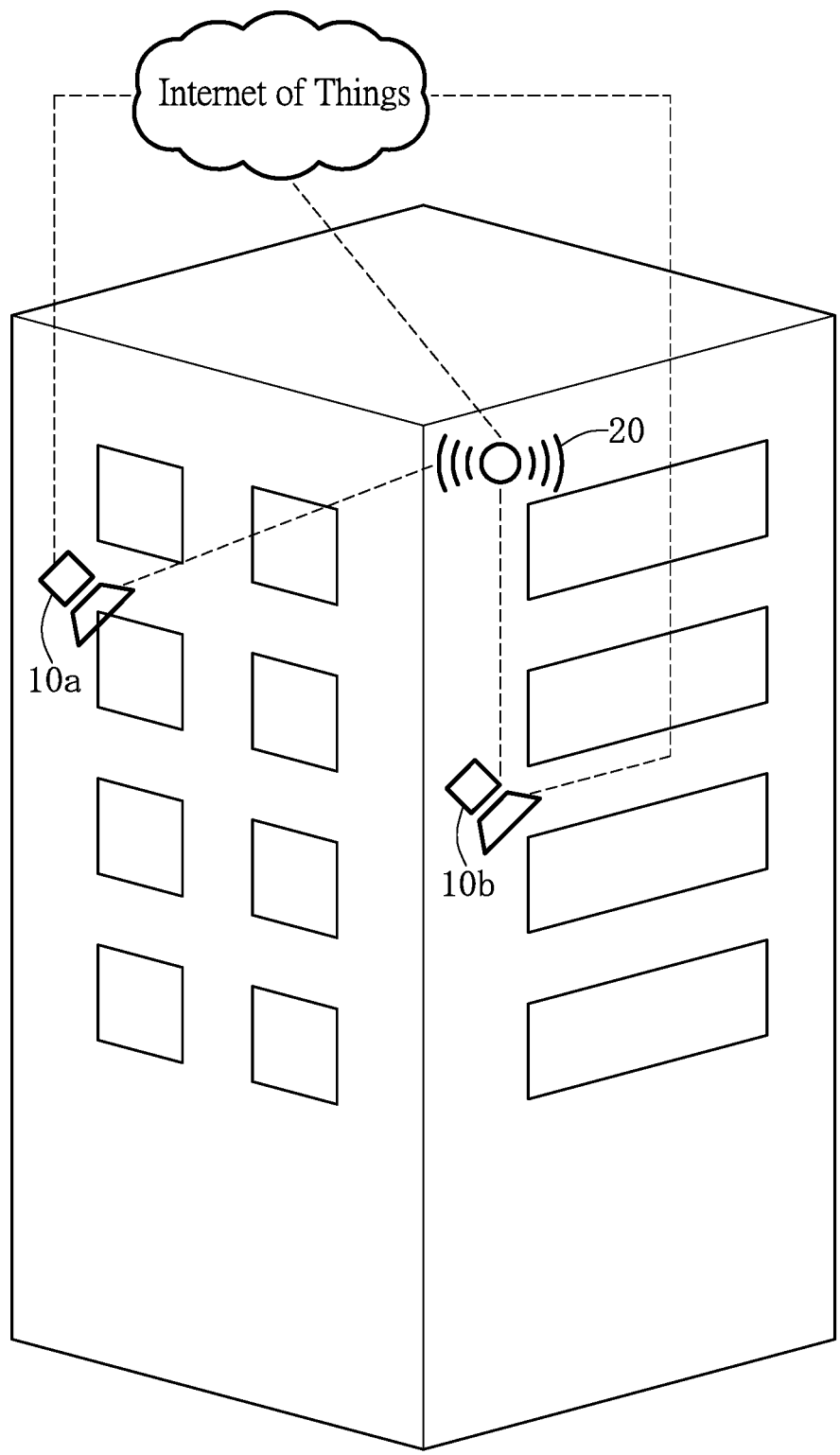
FIG. 3B shows a schematic diagram of the data transmission in a fever epidemic detection system of another embodiment of the instant disclosure.

Refer to FIG. 3A and FIG. 3B. FIG. 3A and FIG. 3B show two schematic diagrams of the data transmission in a fever epidemic detection system of embodiments of the instant disclosure.

The reason why the fever epidemic detection systems 1 and 2 in the above embodiments have no landform or space constraints is that, the data transmission can be implemented via different communication ways in the fever epidemic detection systems 1 and 2. The following descriptions illustrate the data transmission in a fever epidemic detection system provided by the instant disclosure.

As shown in FIG. 3A and FIG. 3B, the fever epidemic detection systems 1 and 2 in the above embodiments can be installed in a plane area, such as the airport lobby, hospital lobby and the like, or can be installed in a multi-story building, such as the multi-story office building, mansion and the like.

No matter the fever epidemic detection systems 1 and 2 a are installed in a plane area or a multi-story building, the measured temperature measured by the detection module 10 and the number of people passing through the detected region during a time interval can, for example, be both transmitted to the control module 20 wirelessly (e.g. via the Zigbee communication). After the control module 20 analyzes and processes the received data, the control module 20 wirelessly (e.g. via the 3G communication) transmits the processed data and the alerting message, if there is, to an external device. For another example, the measured temperature measured by the detection module 10 and the number of people passing through the detected region during a time interval can be both directly transmitted to an external device wirelessly (e.g. via the Wi-Fi communication).

It should be noticed that, the above descriptions are examples only for illustrating but not for restricting the instant disclosure.

In brief, in addition to automatically measuring the temperature of people passing through the detected region, and to transmit the alerting message and the corresponding detailed data to an external device via the Internet of Things (IoT) once there is an person whose temperature is abnormal, the fever epidemic detection system provided by the instant disclosure can also immediately inform a supervisor that the region under detection is safe, possible to be critical or has already been critical. Therefore, it only takes little labor cost for the fever epidemic detection system provided by the instant disclosure to immediately predict the spread of the fever epidemic and further to stop the disease from spreading as soon as possible.

One Embodiment of the Fever Epidemic Detection Method

Figure 4:
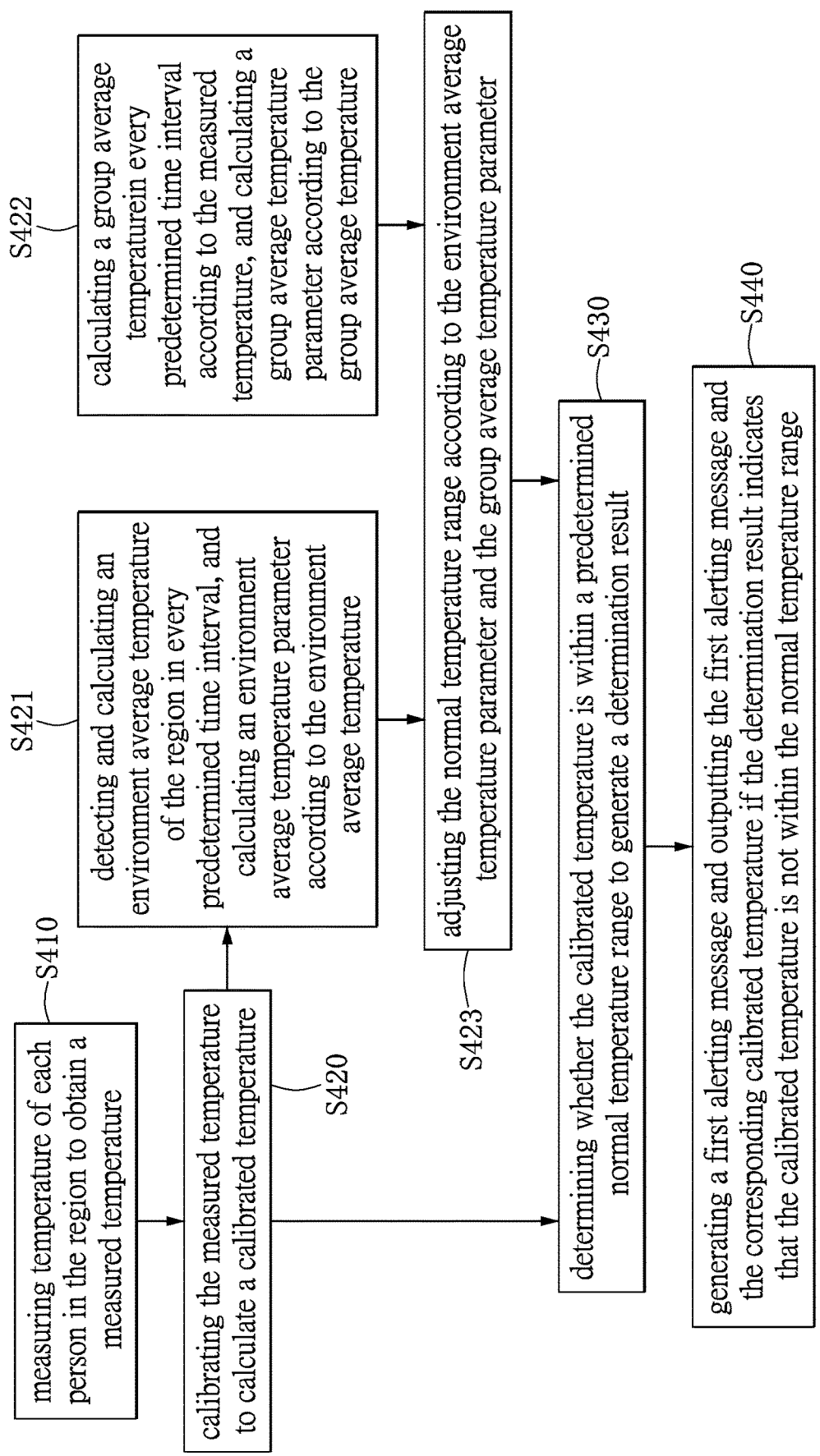
FIG. 4 shows a flow chart of a fever epidemic detection method of one embodiment of the instant disclosure.

Refer to FIG. 4. FIG. 4 shows a flow chart of a fever epidemic detection method of one embodiment of the instant disclosure. Explanatory steps of the present embodiment may be embodied with a fever epidemic detection system 1 in FIG. 1, and thus FIG. 1 is referred for an easy instruction and better understanding.

Again refer to FIG. 1. As mentioned, the fever epidemic detection system 1 comprises a detection module 10, a control module 20 and a communication module 30. The control module 20 is connected to the detection module 10, and the communication module 30 is connected to both of the control module 20 and the detection module 10. The control module 20 further comprises a first operation unit 22, a determination unit 24 and an alert unit 26. The fever epidemic detection method in this embodiment comprises steps as shown in FIG. 4.

In the Step S410, a measuring temperature of each person in the region is measured to obtain a measured temperature. In the Step S420, the measured temperature is calibrated with a calibration factor to calculate a calibrated temperature, wherein the calibration factor is related to the detection module. In the Step S421, an environment average temperature of the region is detected and calculated in every predetermined time interval, and an environment average temperature parameter is further calculated according to the environment average temperature. Simultaneously, in the Step S422, a group average temperature is calculated in every predetermined time interval according to the measured temperature, and then a group average temperature parameter is further calculated according to the group average temperature. After that, in the Step S423, the normal temperature range is adjusted according to the environment average temperature parameter and the group average temperature parameter, and in the Step S430, whether the calibrated temperature is within a predetermined normal temperature range is determined to generate a determination result. Finally, in the Step S440, a first alerting message is generated, and the first alerting message and the corresponding calibrated temperature is outputted if the determination result indicates that the calibrated temperature is not within the normal temperature range.

Another Embodiment of the Fever Epidemic Detection Method

Figure 5A:
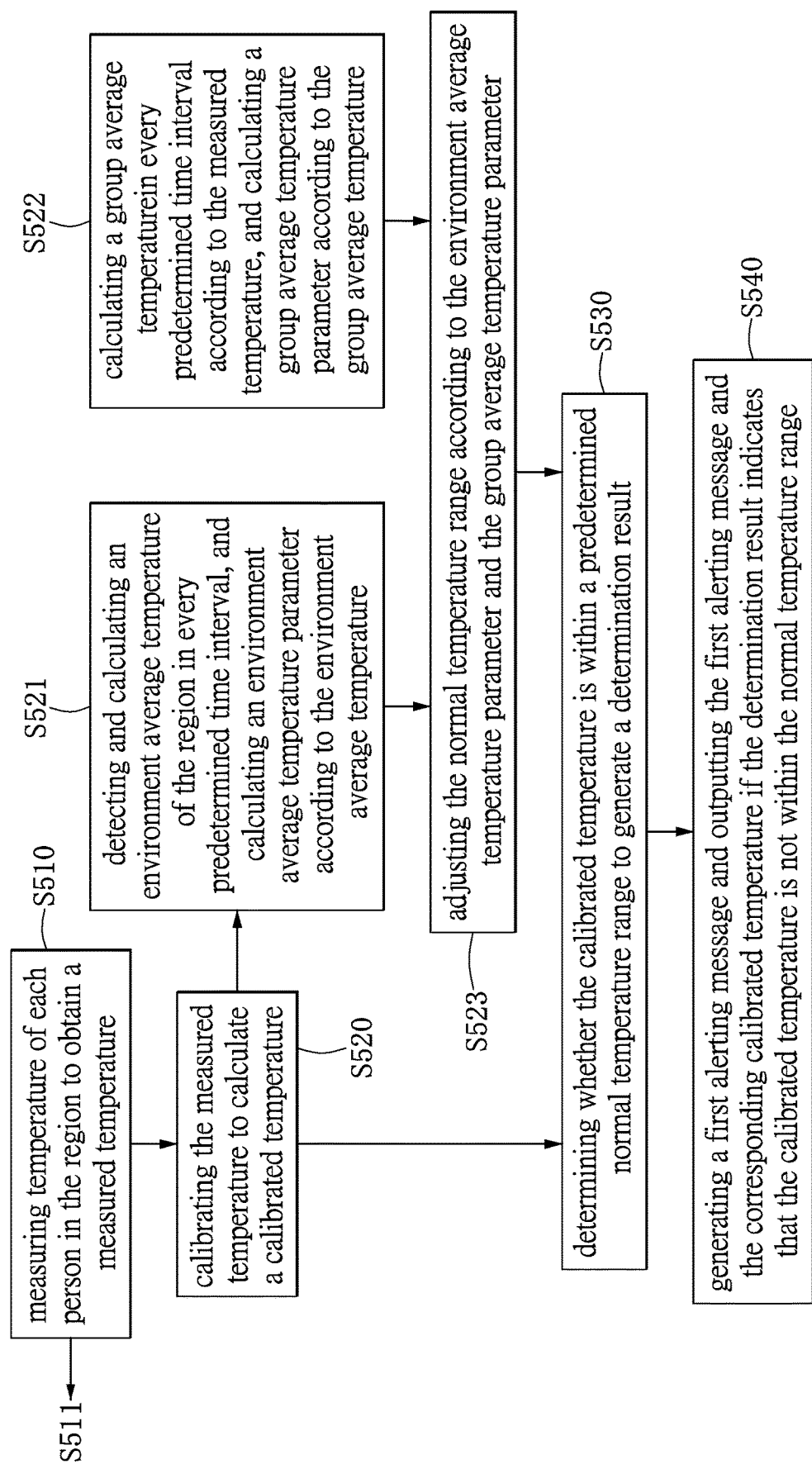
FIGS. 5A and 5B show flow charts of a fever epidemic detection method of another embodiment of the instant disclosure.
Figure 5B:
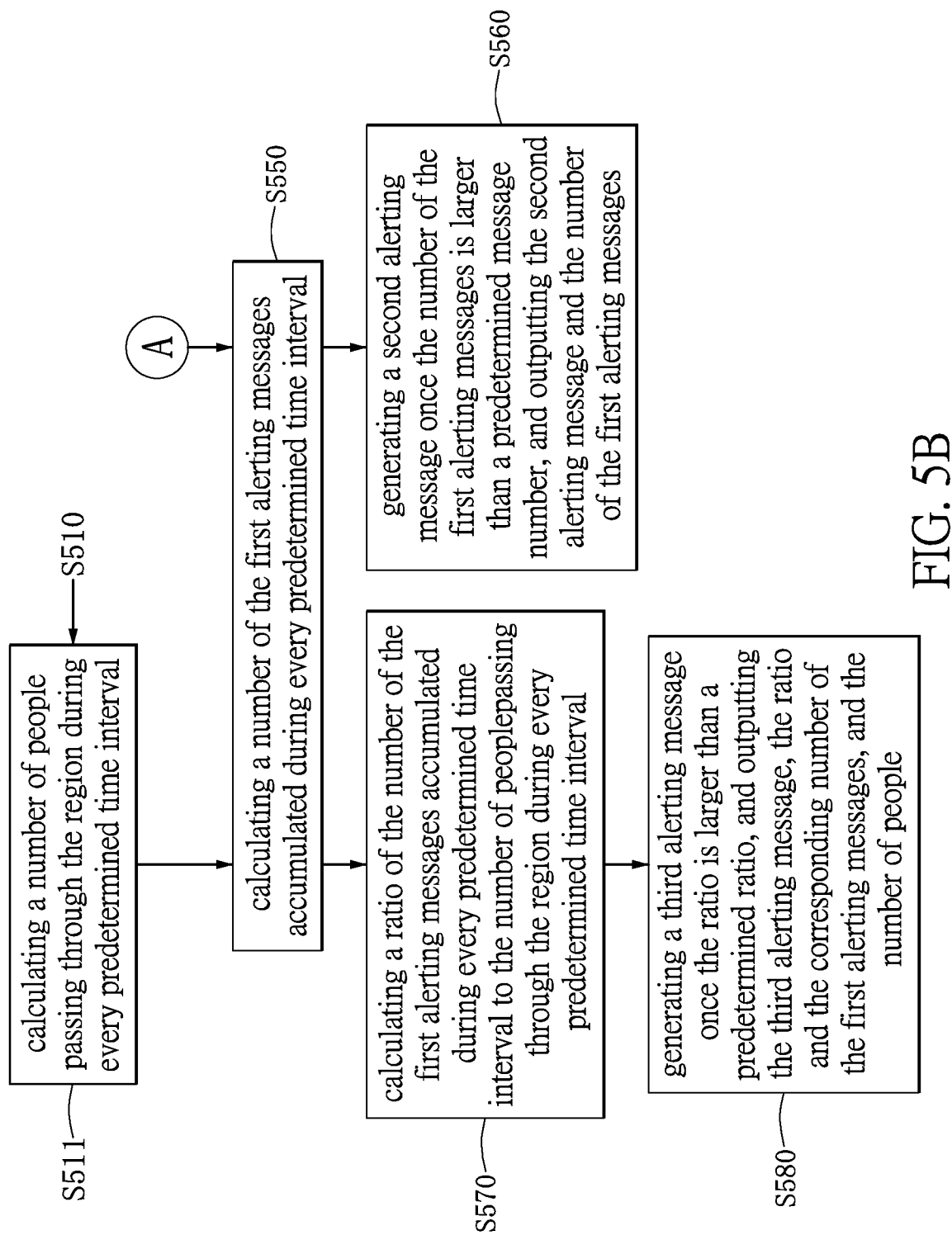

Refer to FIGS. 5A and 5B. FIGS. 5A and 5B show flow charts of a fever epidemic detection method of another embodiment of the instant disclosure. Explanatory steps of the present embodiment may be embodied with a fever epidemic detection system 2 in FIG. 2, and thus FIG. 2 is referred for an easy instruction and better understanding.

Again refer to FIG. 2. As mentioned, the fever epidemic detection system 2 comprises a detection module 10, a control module 20 and a communication module 30. The control module 20 is connected to the detection module 10, and the communication module 30 is connected to the control module 20 and the detection module 10. The control module 20 further comprises a sensing unit 21, a first operation unit 22 and a second operation unit 28, a determination unit 24, and an alert unit 26. The fever epidemic detection method in this embodiment comprises steps as shown in FIGS. 5A and 5B.

In the Step S510, the temperature of each person in the region is measured to obtain a measured temperature, and in the Step S511, the number of people passing through the region is calculated during every predetermined time interval. In the Step S520, the measured temperature is calibrated with a calibration factor to calculate a calibrated temperature, wherein the calibration factor is related to the detection module. After that, in the Step S521, an environment average temperature of the region is detected and calculated in every predetermined time interval, and then an environment average temperature parameter is further calculated according to the environment average temperature. Simultaneously, in the Step S522, a group average temperature is calculated in every predetermined time interval according to the measured temperature, and then a group average temperature parameter is further calculated according to the group average temperature. After the Step S521 and the Step S522, in the Step S523, the normal temperature range is adjusted according to the environment average temperature parameter and the group average temperature parameter. In the Step S530, whether the calibrated temperature is within a predetermined normal temperature range is determined to generate a determination result, and then in the Step S540, a first alerting message is generated, and the first alerting message and the corresponding calibrated temperature are outputted if the determination result indicates that the calibrated temperature is not within the normal temperature range.

In the Step S550, the number of the first alerting messages generated in the Step S540 accumulated during every predetermined time interval is calculated. At last, in the Step S560, a second alerting message is generated once the number of the first alerting messages calculated in the Step 550 is larger than a predetermined message number, and then the second alerting message and the number of the first alerting messages are outputted. On the other hand, in the Step S570, a ratio of the number of the first alerting messages accumulated during every predetermined time interval calculated in the Step S550 to the number of people passing through the detected region calculated in the Step S511 during every predetermined time interval is calculated. Finally, in the Step S580, a third alerting message is generated once the ratio calculated in the Step S570 is larger than a predetermined ratio, and then the third alerting message, the ratio and the corresponding number of the first alerting messages, and the number of people passing through the detected region during a predetermined time interval are outputted.

To sum up, via the combination of the detection module (e.g. a thermal imager), the control module and the Internet of Things (IoT), the fever epidemic detection system and the method thereof provided by the instant disclosure can not only automatically detect the temperatures of people, but also can simultaneously execute the data operation and determine whether there is any abnormal situation. In addition, the fever epidemic detection system and the method thereof can transmit the alerting message indicating the abnormal situation and the corresponding data to an external device via the IoT. Thereby, the supervisor can know in real time that the region under detection is safe, is possible to be or has already been critical. In other words, it only takes little labor cost for the fever epidemic detection system and the method thereof provided by the instant disclosure to immediately predict the spread of the fever epidemic and to further stop the disease from spreading as soon as possible.

The descriptions illustrated supra set forth simply the preferred embodiments of the instant disclosure; however, the characteristics of the instant disclosure are by no means restricted thereto. All changes, alterations, or modifications conveniently considered by those skilled in the art are deemed to be encompassed within the scope of the instant disclosure delineated by the following claims.

What is claimed is:

1. A fever epidemic detection method, used in a fever epidemic detection system for automatically and widely detecting fever epidemic in a region via Internet of Things ("IoT"), comprising:
   calculating a number of people passing through the region during a predetermined time interval;
   detecting temperature of the region in the predetermined time interval to obtain an environment average temperature and calculating an environment average temperature parameter according to the environment average temperature;
   using a thermal imager to measure temperature of each person in the region to obtain a measured temperature;
   calibrating the measured temperature with a calibration factor to calculate a calibrated temperature, wherein the calibration factor is with respect to a type of the thermal imager;
   determining whether the calibrated temperature is within a predetermined normal temperature range so as to generate a determination result;
   generating a first alerting message and outputting the first alerting message and a corresponding calibrated temperature if the determination result indicates that the calibrated temperature is not within the normal temperature range, and transmitting the first alerting message and the corresponding calibrated temperature to an external device;
   counting a number of the first alerting messages accumulated during the predetermined time interval and calculating a ratio of the number of the first alerting messages to the number of people passing through the region during the predetermined time interval
   generating a third alerting message once the ratio is larger than a predetermined ratio; and
   transmitting the third alerting message, the ratio, the corresponding number of the first alerting messages, and the number of people to the external device;
   wherein the third alerting message indicates that among people who have passed through the region during the predetermined time interval, the people whose temperatures are abnormal are equal to or more than a certain percentage of the people who have passed through the region.

2. The fever epidemic detection method according to claim 1, further comprising:
   calculating a group average temperature in every predetermined time interval according to the measured temperature, and calculating a group average temperature parameter according to the group average temperature; and
   adjusting the normal temperature range according to the environment average temperature parameter and the group average temperature parameter.

3. The fever epidemic detection method according to claim 1, further comprising:
   wherein a second alerting message is generated once the number of the first alerting messages is larger than a predetermined message number, and the second alerting message and the number of the first alerting messages are outputted.

* * * * *